(12) United States Patent
Oebbeke

(10) Patent No.: US 12,121,942 B2
(45) Date of Patent: Oct. 22, 2024

(54) CLEANING AND/OR DISINFECTING DEVICE

(71) Applicant: OLYMPUS Winter & Ibe GmbH, Hamburg (DE)

(72) Inventor: Dirk Oebbeke, Bad Oeynhausen (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 317 days.

(21) Appl. No.: 17/752,043

(22) Filed: May 24, 2022

(65) Prior Publication Data
US 2022/0379353 A1    Dec. 1, 2022

(30) Foreign Application Priority Data

May 27, 2021   (DE) ..................... 10 2021 113 643.1
May 17, 2022   (EP) .................................. 22 173 873

(51) Int. Cl.
*B08B 3/04*        (2006.01)
*A61L 2/26*        (2006.01)

(52) U.S. Cl.
CPC   *B08B 3/04* (2013.01); *A61L 2/26* (2013.01); *A61L 2202/122* (2013.01); *B08B 2203/00* (2013.01)

(58) Field of Classification Search
CPC ....................................................... B08B 3/04
See application file for complete search history.

(56) References Cited

FOREIGN PATENT DOCUMENTS

| DE | 10 2017 129 860 A1 | 6/2019 |
| EP | 0 432 281 B1 | 10/1994 |
| EP | 2 604 296 A1 | 6/2013 |
| EP | 3 409 824 B1 | 9/2019 |
| JP | 2002/253466 A | 9/2002 |

*Primary Examiner* — Jason Y Ko
(74) *Attorney, Agent, or Firm* — Scully, Scott, Murphy & Presser, P.C.

(57) ABSTRACT

A cleaning and/or disinfecting device, including: a rinsing container having a rinsing chamber, the rinsing container having a loading opening for loading with washware to be cleaned; a rinsing chamber door, by which the loading opening can be closed in a fluid-tight manner, wherein the rinsing chamber door is a lift door configured to be displaceable translationally in a height direction of the rinsing container; and a drip collector arranged below the rinsing container in the height direction, the drip collector being configured to be displaced translationally in a direction running transversely to the height direction of the rinsing container, the drip collector being configured to be transitioned from a non-use position overlapping with the rinsing container to a use position protruding past the rinsing container on a loading opening side and from the use position back to the non-use position.

20 Claims, 9 Drawing Sheets

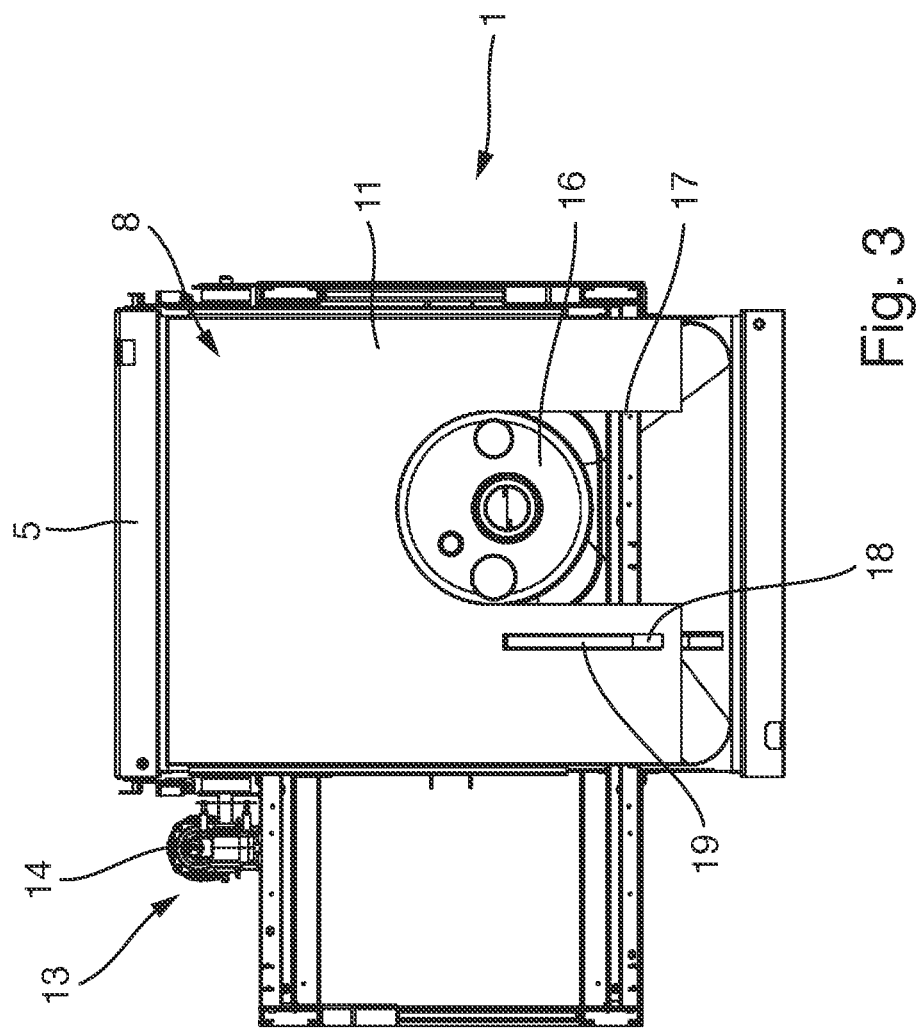

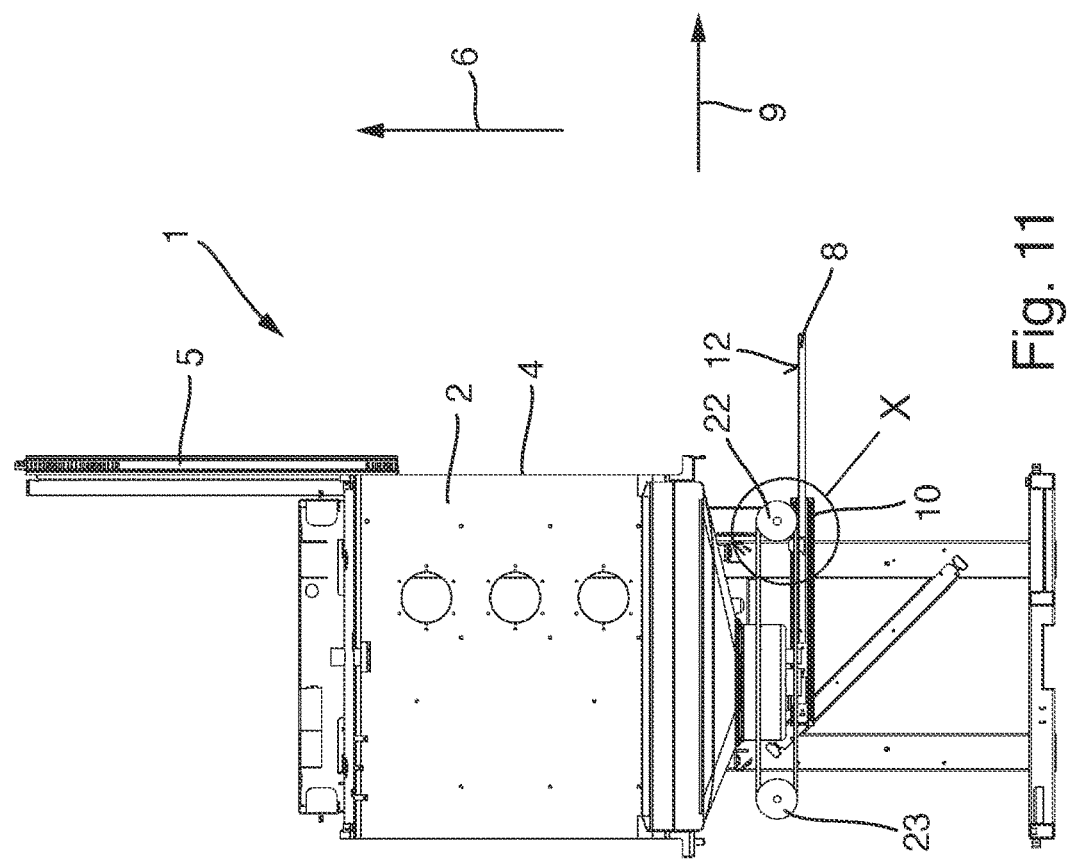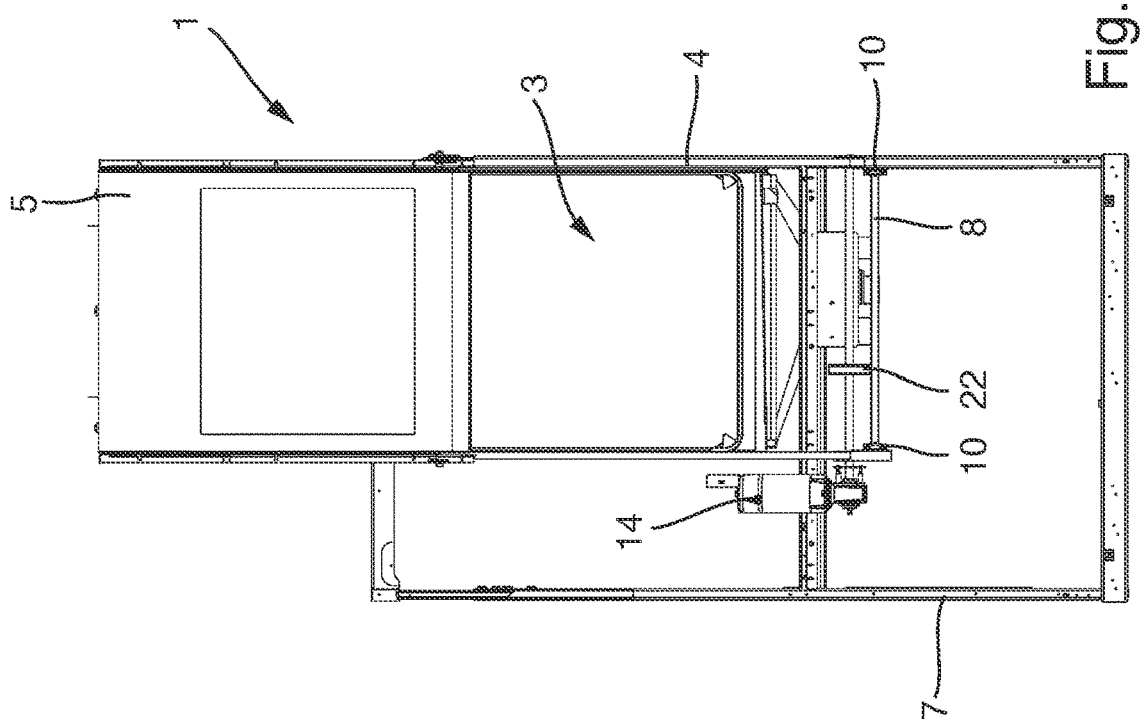

CLEANING AND/OR DISINFECTING DEVICE

CROSS-REFERENCE TO RELATED APPLICATION

The present application is based upon and claims the benefit of priority from DE 10 2021 113 643.1 filed on May 27, 2021, and EP 22 173 873.5 filed on May 17, 2022, the entire contents of each of which is incorporated herein by reference.

BACKGROUND

Field

The present disclosure relates to a cleaning and/or disinfecting device, such as a rinsing machine, with a rinsing container providing a rinsing chamber, which container has a loading opening for loading with washware to be cleaned, as well as with a rinsing chamber door, by which the loading opening can be closed in a fluid-tight manner, wherein the rinsing chamber door is a lift door configured to be displaceable translationally in the height direction of the rinsing container.

Furthermore, the present disclosure relates to a use of a cleaning and/or disinfecting device.

Prior Art

Cleaning and/or disinfecting devices of the previously mentioned type are known per se from the prior art, which is why a separate mention of a publication is not required at this point. Therefore, reference is also made only by way of example to EP 2 604 296 A1.

Previously known cleaning and/or disinfecting devices—also known as CDDs for short—typically have a rinsing container which provides for its part a rinsing chamber for receiving washware to be cleaned and/or disinfected. For the purpose of loading the rinsing chamber with washware to be cleaned and/or to be disinfected, the rinsing container has a loading opening. This can be closed in a fluid-tight manner by a rinsing chamber door configured as a lift door.

The lift door of the cleaning and/or disinfecting device previously known from the aforementioned EP 2 604 296 A1 can be displaced translationally in the height direction of the rinsing chamber and with regard to the loading opening can be brought from a closed position to an open position and vice versa. In doing so, the lift door is displaced in the proper use case by a motor, for which purpose a correspondingly configured drive device is provided.

A fundamental problem with cleaning and/or disinfecting devices of the generic type is that, when the lift door is in the open position, there is a danger that residual liquids can drip from the lift door itself and/or from washware carriers extending out of the rinsing container, which leads to a wet and dirty floor region in front of the cleaning and/or disinfecting device at the location of installation of the cleaning and/or disinfecting device. This is problematic not only for hygienic reasons but also presents a safety risk for a user, since wet floor regions directly in front of the cleaning and/or disinfecting device present a risk of slipping for users. With cleaning and/or disinfecting devices with rinsing chamber doors that are mounted pivotably, this problem does not occur, since a rinsing chamber door pivoted into the open position automatically provides drip protection. However, with lift doors that are displaceable vertically in the height direction, this automatic drip protection is not given, which means there is need for improvement in this regard.

SUMMARY

Starting from the above described prior art, an object is to provide a cleaning and/or disinfecting device of the generic type which further develops the configuration with regard to drip protection, wherein it is important to keep the floor region located directly in front of the cleaning and/or disinfecting device at the location of installation of the cleaning and/or disinfecting device largely free from dripping residual liquids and/or other contaminants.

To achieve such object, a cleaning and/or disinfecting device, such as a rinsing machine, is provided, with a rinsing container providing a rinsing chamber, which container has a loading opening for loading with washware to be cleaned, as well as with a rinsing chamber door, by which the loading opening can be closed in a fluid-tight manner, wherein the rinsing chamber door is a lift door configured to be displaceable translationally in the height direction of the rinsing container, wherein a drip collector is arranged below the rinsing container in the height direction and is configured to be displaceable translationally in a direction running transversely to the height direction of the rinsing container, and the drip collector can be transitioned from a non-use position overlapping with the rinsing container to a use position protruding past the rinsing container on the loading opening side and vice versa.

The cleaning and/or disinfecting device can have a drip collector. This serves to be able to catch liquids and/or contaminants dripping from the lift door and/or from washware carriers displaced out of the rinsing container when the lift door is in the open position. Thus, the floor region in the direct vicinity in front of the cleaning and/or disinfecting device is protected from dripping residual liquids and/or contaminants, meaning this region remains free of dripping residual liquids and/or contaminants. In contrast to the prior art, this allows a much more hygienic operation and also reduces the risk of injury which otherwise exists due to an existing danger of slipping.

The cleaning and/or disinfection device can be provided for the reprocessing of surgical instruments, such as endoscopes or the like, wherein the rinsing chamber can be configured to accommodate one or more surgical instruments, for example, arranged in receiving baskets. In order to connect the channels of the surgical instruments with a rinsing circuit of the cleaning and/or disinfection device, such as reprocessing device, the receiving baskets for the surgical instruments, in which the endoscopes to be cleaned are respectively arranged, can have adapters for the channels of the surgical instruments, such as endoscopes, etc. As a result, when a receiving basket with a surgical instrument to be cleaned, such as an endoscope, is introduced into the rinsing chamber of the reprocessing unit or the cleaning and/or disinfecting device, the channels of the surgical instrument can be connected to rinsing channels of the rinsing circuit or the adapter can be connected to a counterpart of the rinsing circuit. For cleaning and disinfection of the surgical instruments, the channels of the surgical instruments, such as endoscopes, can be flushed with a reprocessing fluid or with rinsing, cleaning and/or disinfection fluids.

As a result, a cleaning and/or disinfecting device with improved handling is thus provided, because it is no longer necessary for the user to manually keep the floor region in front of the cleaning and/or disinfecting device clean with corresponding cleaning activities. By the drip collector provided, any residual liquids and/or contaminants dripping from the lift door or from the washware carriers, for example, receiving baskets for surgical instruments arranged therein, extending out of the rinsing chamber are caught and centrally collected and/or discharged.

The drip collector can be arranged below the rinsing container in the height direction and can be configured to be displaceable in a direction running transversely to the height direction of the rinsing container. The drip collector can be transitioned from a non-use position overlapping with the rinsing container to a use position protruding past the rinsing container on the loading opening side and vice versa.

The drip collector can be arranged outside of the rinsing chamber provided by the rinsing container, namely below the rinsing container. In case of need, the drip collector can be transitioned from a non-use position to a use position and vice versa, wherein the drip collector can be displaced linearly, in a direction running transversely to the height direction of the rinsing container.

In the non-use position, the drip collector can overlap with the rinsing container, meaning the drip collector can be arranged directly beneath the rinsing container in this position and does not protrude past it. Completely free access to the rinsing container is thus ensured.

To transition the drip collector to the use position, it can be displaced linearly, in the direction of the loading opening-side wall of the rinsing container. As soon as the drip collector has reached its end position in the use position, the drip collector can protrude past the rinsing container like a drawer, on the loading opening side. With that, the floor at the location of installation which is located directly in front of the cleaning and/or disinfecting device is in the shadow of the drip collector so that dripping residual liquids and/or contaminants do not fall onto the floor but rather onto the drip collector. Consequently, the floor directly underneath is protected from dripping residual liquids and/or falling contaminants and/or like contaminants by the drip collector.

According to another feature, it is provided that the drip collector can have a plate-shaped element. The drip collector can be configured as a plate. A structure that is flat overall in the height direction is thus given, which enables a space-saving arrangement of the drip collector below the rinsing container.

According to another feature, the large side, facing the rinsing container, of the flat element can have a slope. This ensures that any drips and/or contaminants caught by the drip collector can be automatically, meaning under the effect of gravity, transported away by following the slope. In this case, at least in the non-use position, a device can be located on the drip collector, by which residual moisture and/or contaminants discharged in correspondence with the slope can be conveyed away and/or supplied to a wastewater pump provided anyway by the cleaning and/or disinfecting machine.

According to another feature, the drip collector can be configured as a type of trough, wherein the flat element can have a border strip on the rinsing chamber side.

This embodiment ensures that the drip collector provides a certain receiving capacity so that an edge-side overflowing of moisture or dirt is effectively prevented.

According to another feature, the drip collector can be mounted displaceably by ball roller pull-outs. This embodiment ensures a secure and smooth displacement movement of the drip collector and ensures a long service life. In addition, precise guidance of the drip collector is ensured.

According to another feature, the drip collector can be manually displaceable. Consequently, it can be taken into use and transitioned from the use position to the non-use position or respectively vice versa selectively by the user. In doing so, the drip collector can be grasped by the user and selectively displaced translationally like a drawer, meaning extended or respectively retracted.

According to another feature, the drip collector can be displaced by a motor. According to this embodiment, an electric motor drive can be provided for the drip collector so that extending or respectively retracting the drip collector by the movement of a motor is permitted. Such a displacement can take place either automatically depending on the position of the lift door or independently therefrom, meaning selectively by the user.

According to another feature, the drip collector can be in operative connection with a motor device that can be operated separately by the user. According to this embodiment, a displacement of the drip collector can take place independently of the position of the lift door. For this purpose, a motor device provided separately for the drip collector can be configured. This motor device can be operated selectively by the user, for which purpose a corresponding operating unit is provided.

According to another feature, the lift door can be displaced by a motor, for which purpose a motor unit can be provided that is in operative connection with the lift door. According to this embodiment, no manual movement of the lift door from the closed position to the open position and vice versa takes place; instead, an electric motor drive is provided. The user can selectively initiate a movement of the lift door via the electric motor unit virtually at the push of a button.

The drip collector can be in operative connection with the motor unit of the lift door. Accordingly, the motor unit which can be already provided for the lift door can also be used to be able to displace the drip collector. Since the lift door, on the one hand, and the drip collector, on the other hand, can use one and the same motor unit or respectively are in operative connection with it, a forced coupling of the lift door and drip collector can be provided. This forced coupling causes the drip collector to also be automatically displaced when the lift door is displaced. In this regard, a user is not required to manually intervene.

In this case, when the lift door is transitioned from the closed position to the open position, the drip collector can automatically extend and form a drip protection in the manner already described previously. If the lift door is displaced back, on the other hand, from the open position to the closed position, the drip collector can also be displaced back to its non-use position, in which it can be arranged directly below the rinsing container in a parked position.

According to another feature, the motor unit of the lift door can have an electric motor and a drive shaft interacting with it, wherein the drive shaft can interact with a force transmission member having a driver.

The motor unit provided for the lift door can have an electric motor and a drive shaft. In the proper use case, the drive shaft can be set in a rotating motion by the electric motor. The drive shaft, for its part, in turn can interact with a force transmission member which can be, for example, a belt, such as a V-belt or a toothed belt, or a chain. This force transmission member can have a driver which can in turn interact with the drip collector. In this manner, a force-transmitting coupling between the electric motor of the motor unit on the one hand and the drip collector on the other hand can be implemented so that, in operation of the electric motor of the motor unit, the drip collector can be displaced. In this case, the drip collector can travel either from the use position to the non-use position or vice versa, depending on the direction of rotation of the electric motor.

According to another feature, the driver can engage in a form-fitting manner with a receiver provided by the drip collector. In this manner, the forced coupling between the driver on the one hand and the drip collector on the other is given. In this case, this operative connection can be configured in a form-fitting manner, which can enable a simple installation in the case of repair.

According to another feature, the receiver can be a slot that has a longitudinal extent exceeding the dimension of the driver in the longitudinal direction. Accordingly, the slot can be configured to be larger in the longitudinal direction than the driver. Thus, an empty slot path can occur, which means that the driver can be initially displaced over a certain distance within the slot before a force-transmitting abutment of the driver on the respective slot end occurs. A type of gear stage can thus be implemented, which can ensure that the lift door is initially displaced over a certain distance in the height direction before the drip collector is driven in turn. Unwanted collisions between the drip collector on the one hand and the lift door on the other can thus be avoided. In addition, this embodiment permits the gear ratio between the driver and the slot as well as the size of the empty path to be set via the size of the driver, depending on the location of installation and user wish. Individual operating requirements can thus be taken into account in an advantageous manner.

According to another feature, a gear arrangement can be provided between the electric motor and the force transmission member. Furthermore, the transmission ratio between a displacement movement of the lift door and a displacement movement of the drip collector can be set and, if applicable, also changed individually later by such a gear arrangement.

As a result, the embodiment can result in an overall cost-effective implementation. The motor drive that can be provided for the lift door can also be used to drive the drip collector in a motorized manner.

The drip collector can be arranged below the rinsing container, meaning not within the rinsing chamber provided by the rinsing container, which can avoid an undesired shadowing inside the rinsing chamber.

Liquid dripping from the lift door and/or washware carriers extending out of the rinsing chamber can be discharged in a simple manner by guide plates or possibly a slight tilt of the drip collector, if applicable in a region of the cleaning and/or disinfecting device which can already be in a flow connection with a conveying device. The washware carriers can be configured as receiving baskets for surgical instruments, such as endoscopes, in each of which at least one surgical instrument for reprocessing can be arranged.

The embodiment can also be independent in principle from the displacement direction of the lift door, so that the drip collector can be used both in combination with such lift doors that are displaced upwards in the height direction for transitioning to the open position and with such lift doors that are displaced downwards in the height direction for transitioning to the open position.

In addition, the drip collector can be arranged below the rinsing container, which in the case of a device configured as a tunnel device enables the drip collector to be able to be displaced either toward one or toward the other side, meaning to what is called the "clean" side or to what is called the "dirty" side.

Furthermore, such object can be solved by a use of a cleaning and/or disinfecting device described above, such as a rinsing machine, for reprocessing at least one surgical instrument, such as an endoscope. To avoid repetition, reference is made expressly to the above explanations.

BRIEF DESCRIPTION OF THE DRAWINGS

Further features will become evident from the description of embodiments, together with the claims and the appended drawings. Embodiments can fulfill individual features or a combination of several features.

The embodiments described below, without restricting the general idea of the invention, based on exemplary embodiments in reference to the drawings, whereby we expressly refer to the drawings with regard to the disclosure of all details that are not explained in greater detail in the text.

Further features and advantages are apparent from the following description with reference to the figures. In the figures

FIG. 3 illustrates a schematic view from below of the cleaning and/or disinfecting device according to FIG. 1;

FIG. 10 illustrates a front view of the cleaning and/or disinfecting device with the lift door completely open;

FIG. 11 illustrates a schematic side view of the cleaning and/or disinfecting device according to FIG. 10;

In the drawings, the same or similar elements and/or parts are, in each case, provided with the same reference numerals such that they are not introduced again in each case.

DETAILED DESCRIPTION

Figure 1:
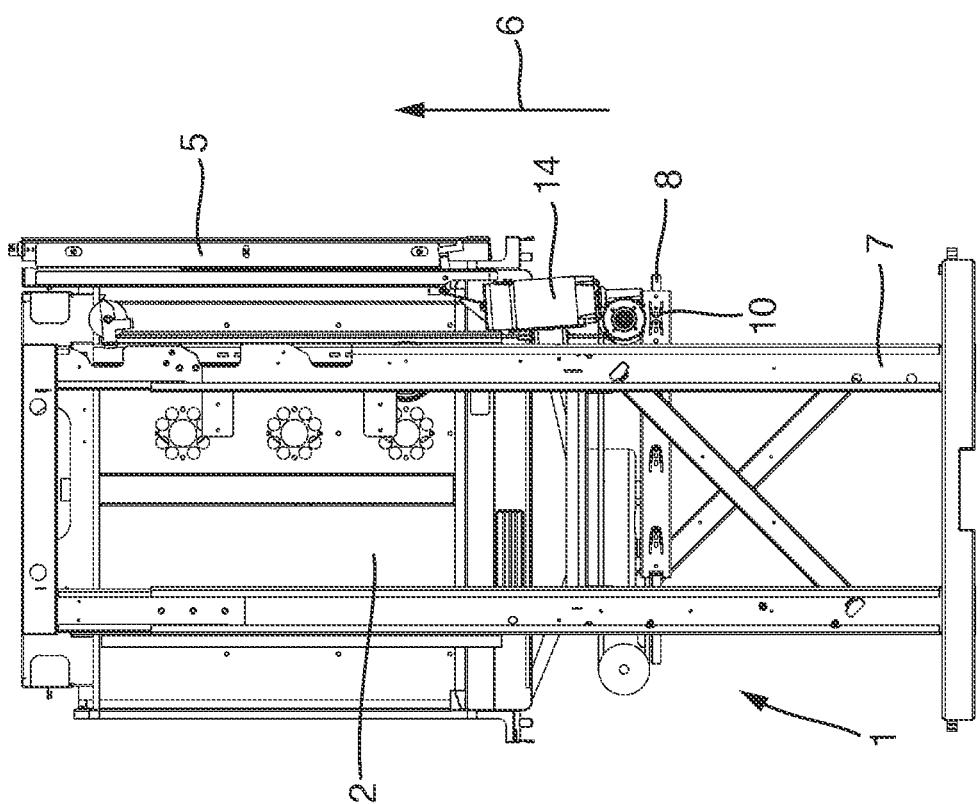
FIG. 1 illustrates a schematic front view of a cleaning and/or disinfecting device.

FIGS. 1 to 17 show a cleaning and/or disinfecting device 1, known as CDD for short, in different views. The cleaning and/or disinfecting device 1 can be configured for reprocessing surgical instruments, such as, endoscopes.

The cleaning and/or disinfecting device 1 has a rinsing container 2 which provides a rinsing chamber 3 for receiving washware to be cleaned and/or disinfected, such as, surgical instruments for example endoscopes. The rinsing chamber 3 is accessible via a loading opening 4, which can be closed in a fluid-tight manner by a lift door 5 that can be displaced translationally in the height direction 6. A frame 7 serves as a carrying support for the rinsing container 2 and the lift door 5 arranged displaceably thereon.

Figure 2:
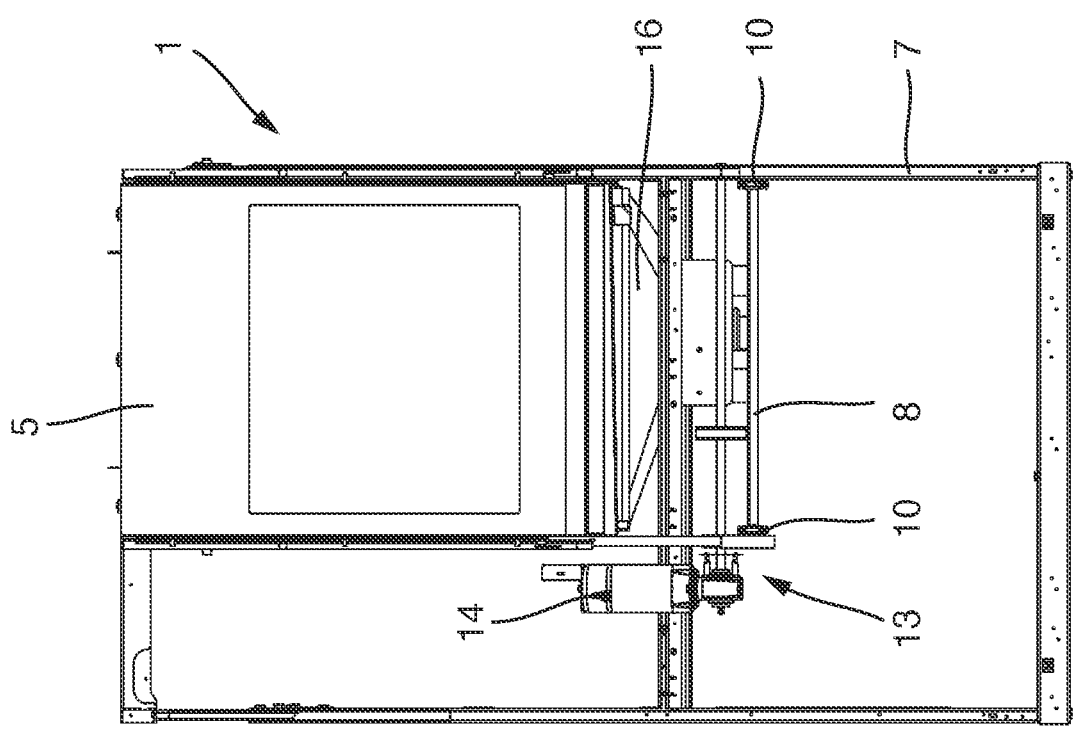
FIG. 2 illustrates a schematic side view of the cleaning and/or disinfecting device according to FIG. 1.
Figure 5:
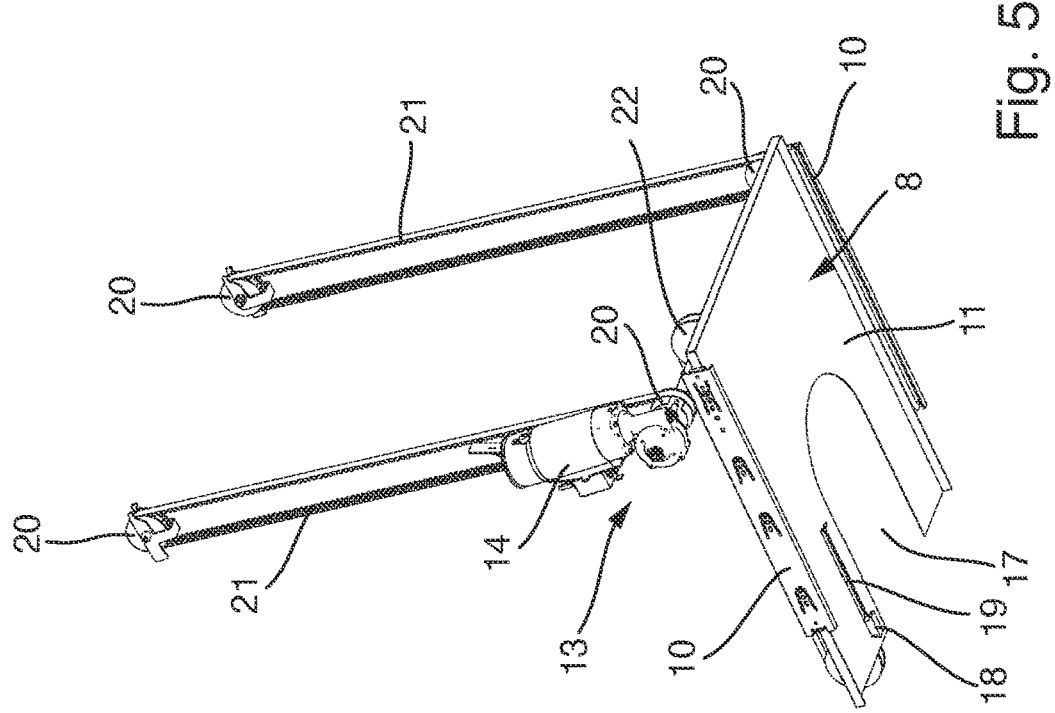
FIG. 5 illustrates a schematic perspective representation from a different viewing angle of the drip collector according to FIG. 4.
Figure 4:
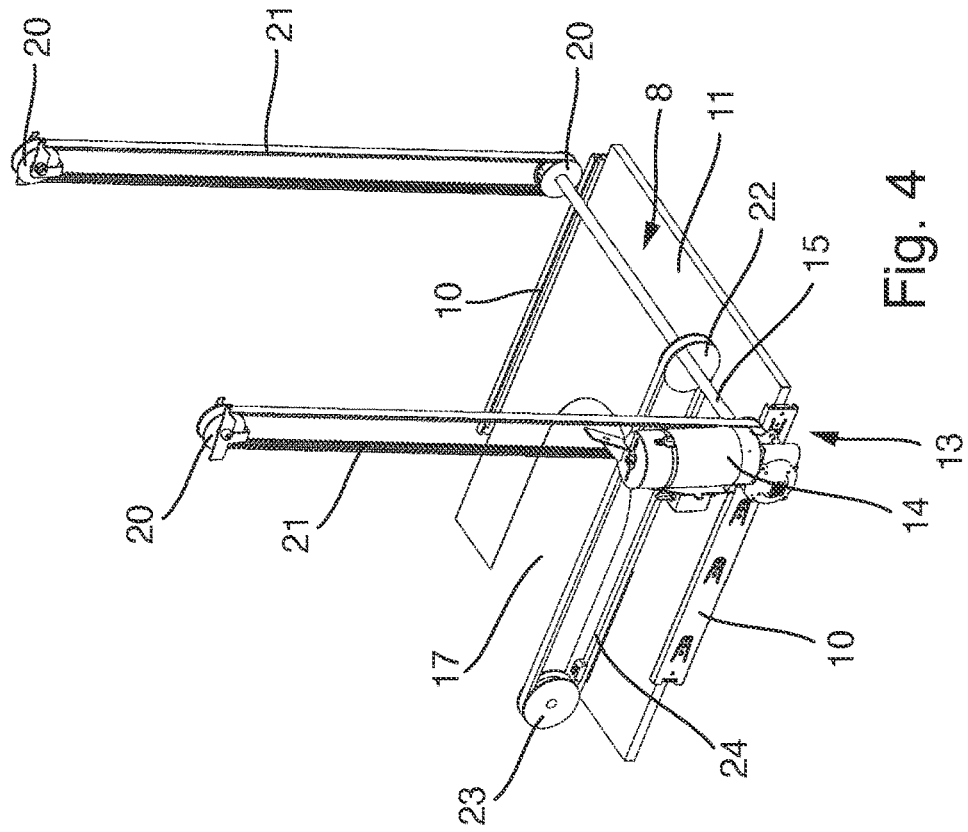
FIG. 4 illustrates a schematic perspective representation of the drip collector including motor unit.
Figure 7:
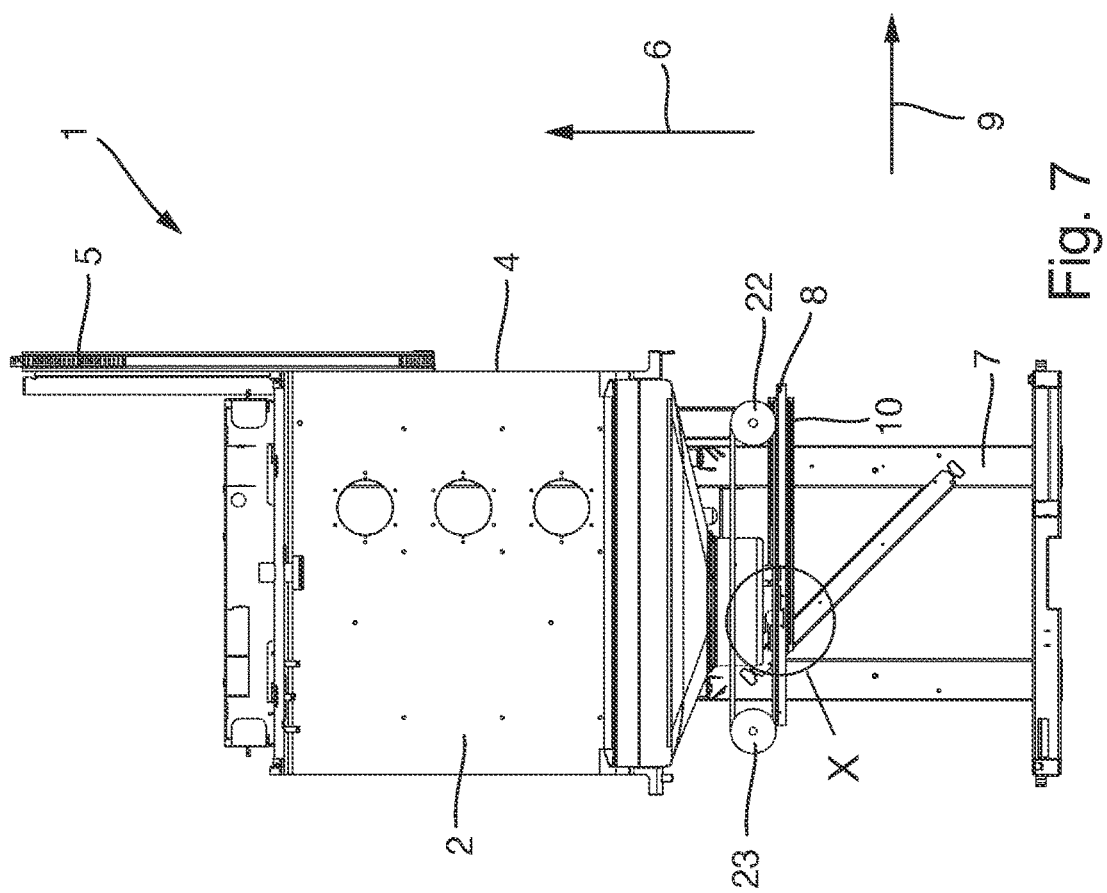
FIG. 7 illustrates a schematic side view of the cleaning and/or disinfecting device according to FIG. 6.
Figure 6:
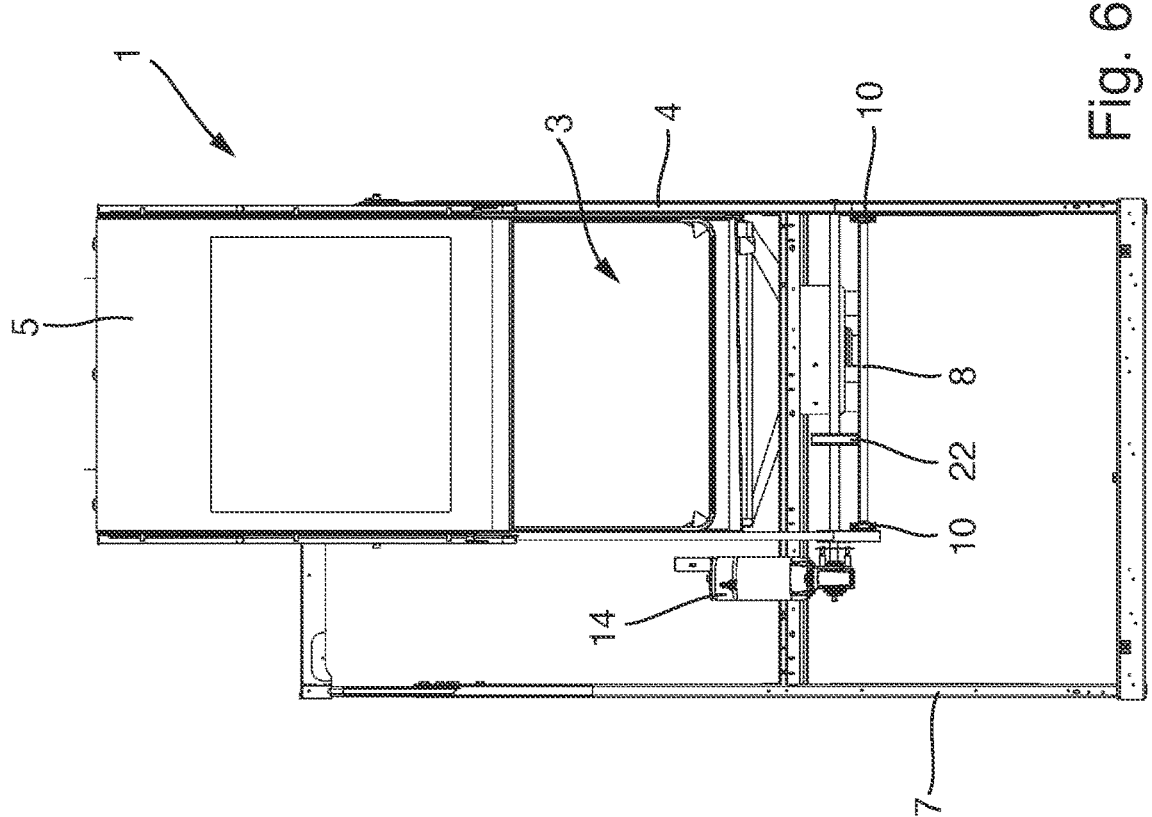
FIG. 6 illustrates a schematic front view of the cleaning and/or disinfecting device with the lift door partially open.

FIGS. 1 to 3 show the cleaning and/or disinfecting device 1 with a lift door 5 located in the closed position. FIGS. 6 to 9 show the cleaning and/or disinfecting device 1 with a partially open lift door 5, meaning a lift door 5 which is partially displaced upwards in the height direction 6. FIGS. 10 to 13 finally show the cleaning and/or disinfecting device 1 with a lift door 5 located in the open position, meaning a lift door 5 which is completely displaced to its open position in the height direction 6.

The cleaning and/or disinfecting device 1 has a drip collector 8. This is arranged below the rinsing chamber 3 in the height direction 6 and is configured as a plate-shaped flat element 11.

The drip collector 8 is mounted to be displaceable translationally by two ball roller pull-outs 10 and is movable in a transverse direction 9 running transversely to the height direction 6. It can be displaced from a non-use position shown in FIGS. 1 to 3 to a use position shown in FIGS. 10 to 13 and vice versa, in the manner of a drawer. To receive the collection pan 16 adjoining the rinsing container 2, the drip collector 8 is equipped with a cut-out 17.

The large side 12, facing the rinsing container 2, of the flat element 11 is configured with a slope so that any drips and/or contaminants caught by the drip collector 8 can flow out in the direction of a central receiver.

The lift door 5 is configured to be displaced with a motor. For this purpose, a motor unit 13 is provided which has an electric motor 14 and a drive shaft 15, as can be seen for example in FIGS. 4 and 5. In the exemplary embodiment shown, the drive shaft 15 is fitted with toothed wheels 20, over each of which a toothed belt 21 is guided, which belt is guided on the other end over frame-side toothed wheels 20. In the proper use case, when the electric motor 14 is started, the drive shaft 15 is rotated, which leads to a driving of the toothed belt 21, which in turn results in a movement of the lift door 5 in the height direction 6.

The linearly displaceable drip collector 8 is in operative connection with the motor unit 13. For this purpose, two wheels 22 and 23 are provided, wherein the wheel 22 is arranged in a rotationally fixed manner on the drive shaft 15. A force transmission member in the form of a V-belt 24 is guided over the two wheels 22 and 23. This belt is equipped with a driver 18 which engages in a recess configured as a slot 19 of the drip collector 8, as can be seen for example in the representation according to FIG. 5. In this manner, a forced coupling between the lift door movement on the one hand and the drip collector movement on the other is given. When transitioning the lift door 5 to the open position, this forced coupling leads to the drip collector 8 being displaced to the right with reference to the drawing plane, for example, according to FIG. 7. When the lift door 5 is transitioned back to the closed position, a displacement movement of the drip collector 8 back to the non-use position, meaning, for example, to the left with reference to the drawing plane according to FIG. 5, takes place.

The slot 19 has a longitudinal extent which exceeds the longitudinal extent of the driver 18. Due to this, an empty path is given, which ensures that a movement of the lift door 5 does not also lead to an immediate movement of the drip collector 8. Rather, the lift door 5 has to first be displaced over a certain distance before the drip collector 8 is then also displaced. In this context, the position of the driver 18 when the lift door 5 is completely closed can be seen in FIG. 3.

After that, the driver 18 lies on the lower edge of the slot 19 with reference to the drawing plane according to FIG. 3.

Figure 9:
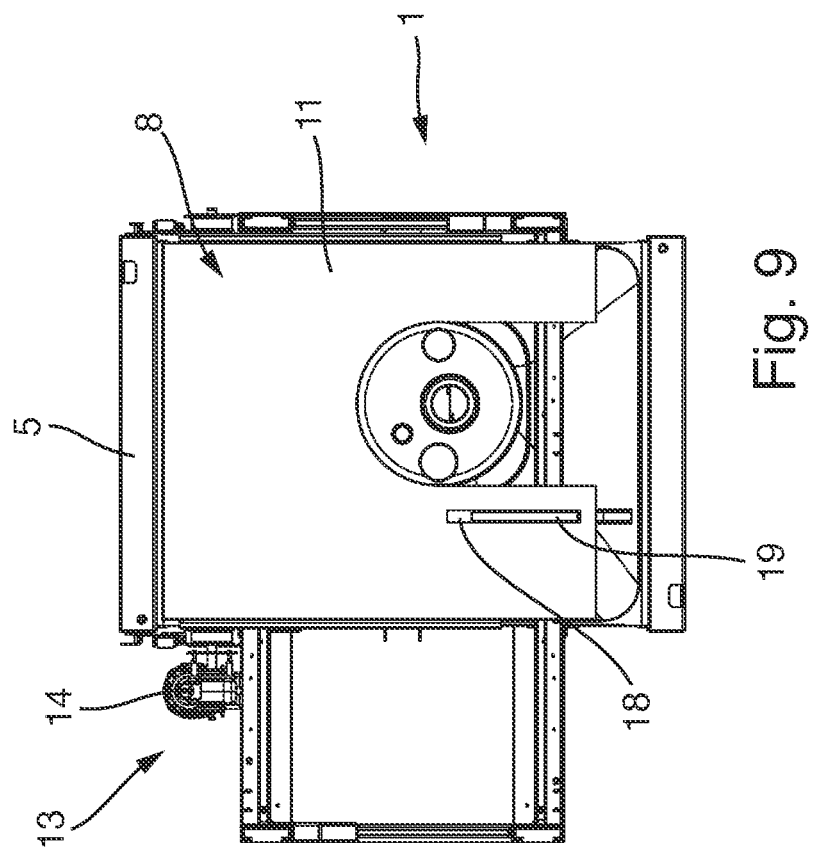
FIG. 9 illustrates a schematic view from below of the cleaning and/or disinfecting device according to FIG. 6.
Figure 8:
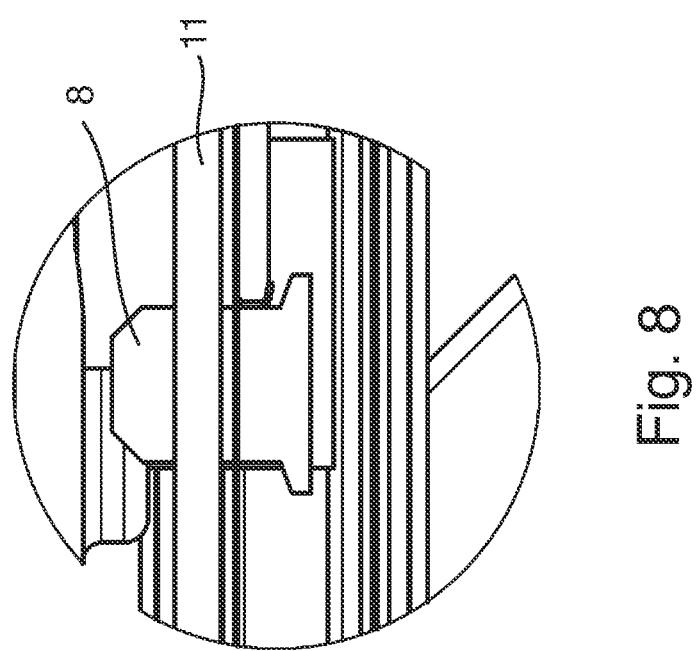
FIG. 8 illustrates a detailed schematic view of the section X according to FIG. 7.

As soon as the lift door 5 is moved to its open position, the driver 18 shifts within the slot 19 until it reaches the position shown in FIG. 9. In this position, the lift door 5 is already somewhat open, but the drip collector 8 has still not moved. The driver 18 now lies on the upper edge of the slot 19 with reference to the drawing plane according to FIG. 9.

Figure 13:
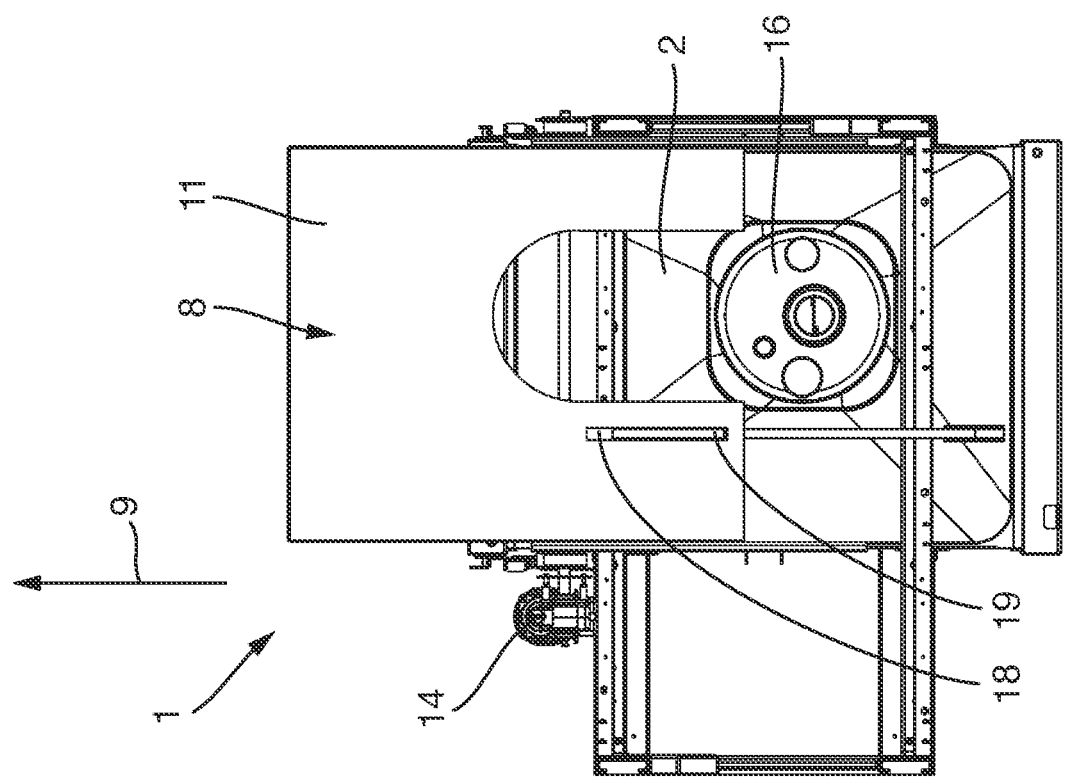
FIG. 13 illustrates a schematic view from below of the cleaning and/or disinfecting device according to FIG. 10.
Figure 12:
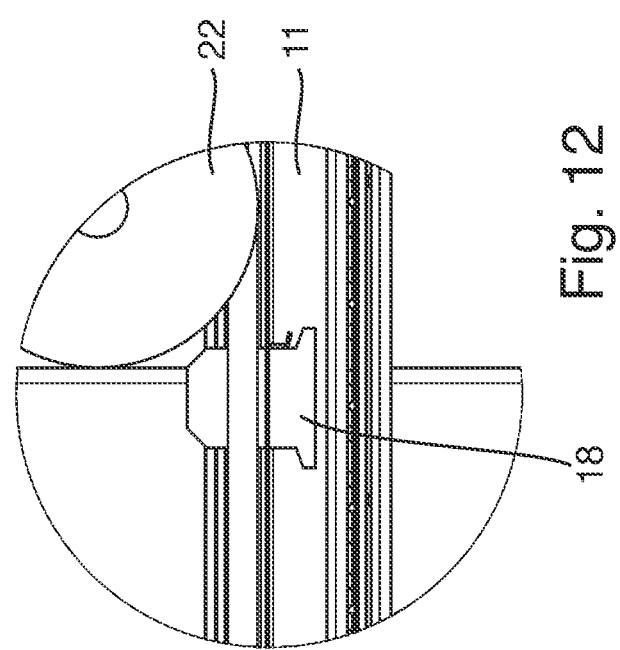
FIG. 12 illustrates a sectional representation of the section X according to FIG. 11.

If the lift door 5 is now displaced further to the completely opened open position in correspondence with FIGS. 10 and 11, the driver 18 now entrains the drip collector 8, as a result of which it is brought to its extended use position, as can be seen for example in FIG. 13.

Figure 14:
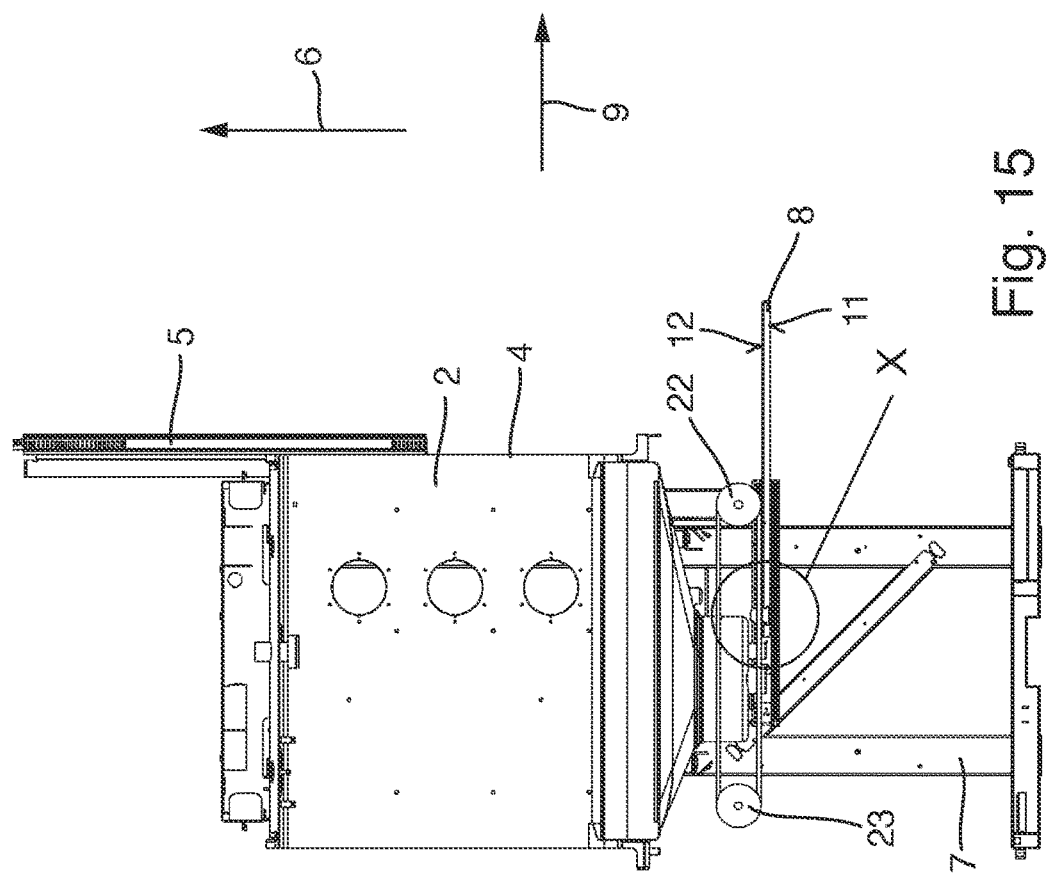
FIG. 14 illustrates a schematic front view of the cleaning and/or disinfecting device with the lift door partially closed.
Figure 15:
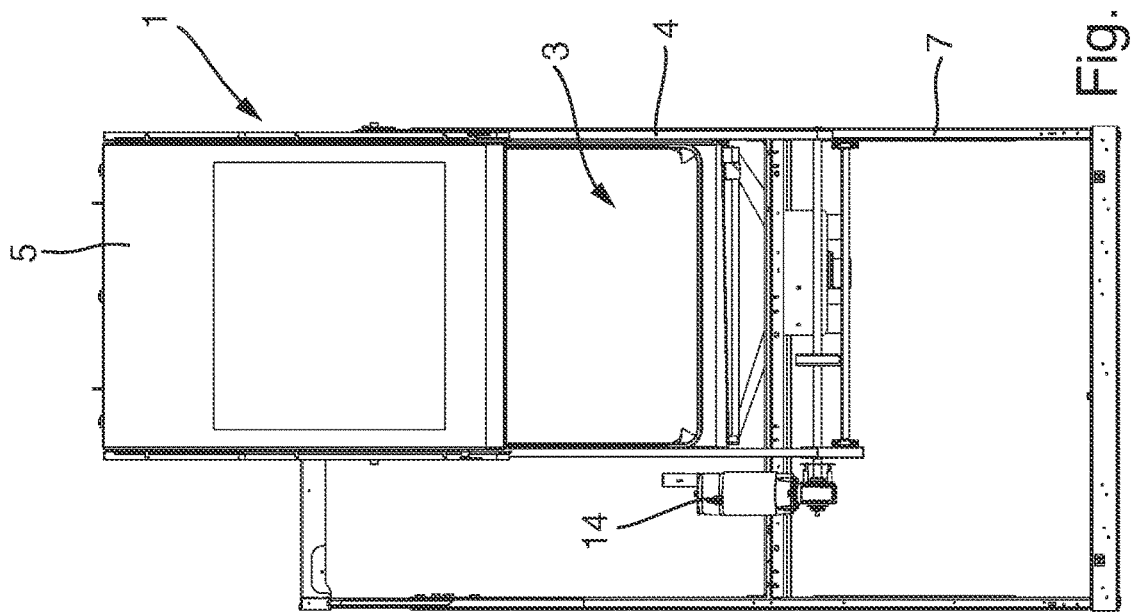
FIG. 15 illustrates a schematic side view of the cleaning and/or disinfecting device according to FIG. 14.
Figure 17:
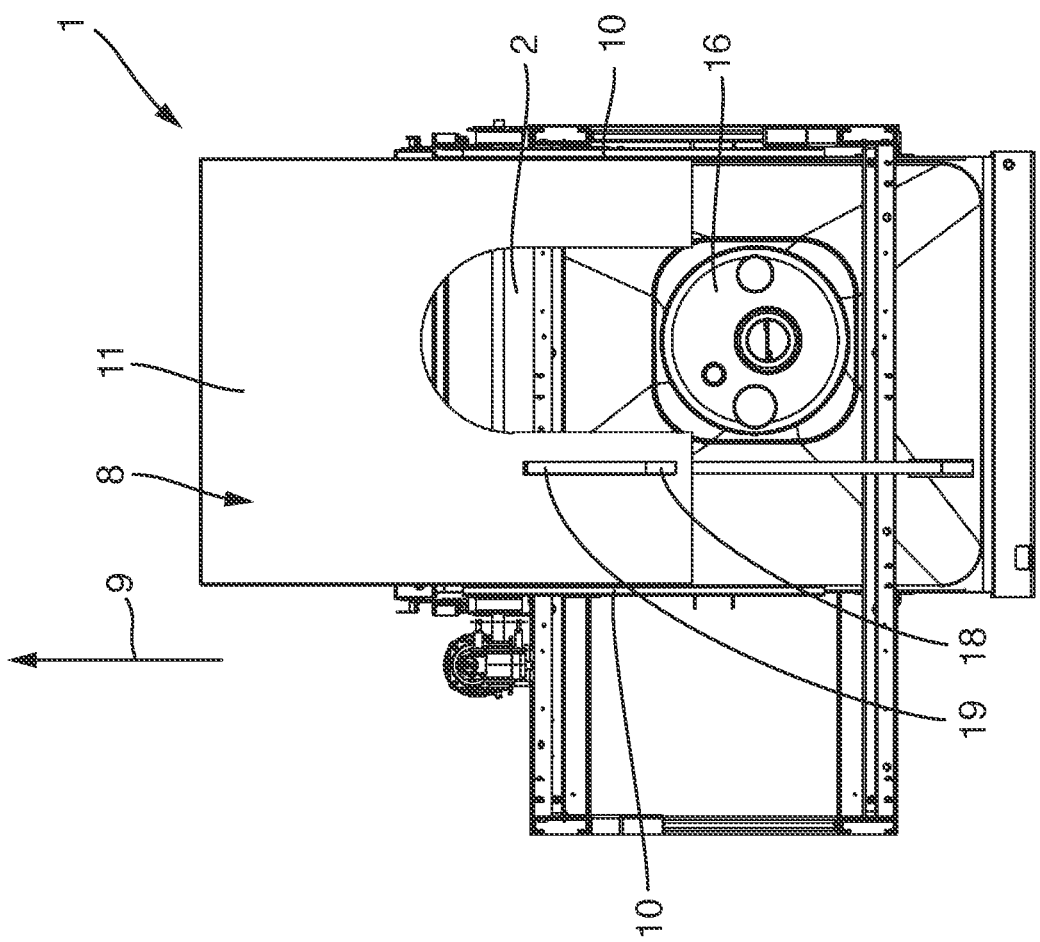
FIG. 17 illustrates a schematic view from below of the cleaning and/or disinfecting device according to FIG. 14.
Figure 16:
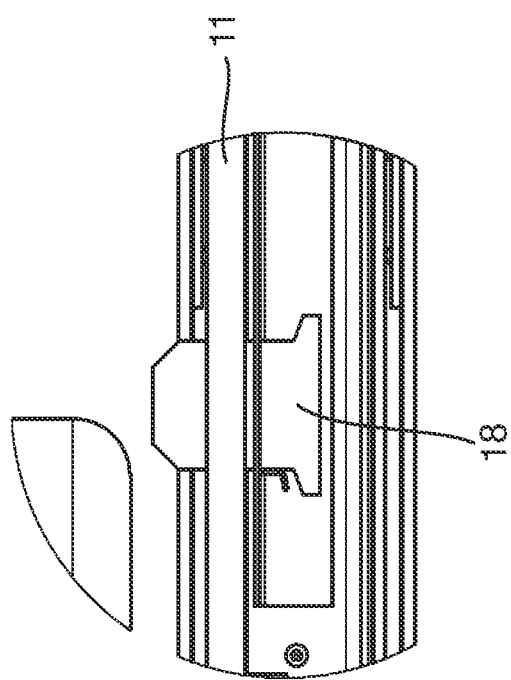
FIG. 16 illustrates a sectional representation of the section X according to FIG. 15

If the lift door 5 is then closed again, meaning brought back to the closed position, the drip collector 8 initially remains in its extended use position, as can be seen in FIGS. 14 and 15. The drip collector 8 remains in this use position until the driver 18 is displaced again within the slot 19 so far that it arrives at the lower edge of the slot 19 with reference to the drawing plane according to FIG. 17.

As soon as this happens, another displacement of the lift door 5 leads to the drip collector 8 being entrained and displaced back to its non-use position according to FIGS. 1 and 2.

As soon as the drip collector 8 is located in its use position, for example, according to FIG. 11, it serves as a drip protection for the floor region located below the drip collector 8. Any residual liquid and/or contaminants dripping from the lift door 5 or from washware carriers extending from the rinsing container under certain circumstances are caught by the drip collector 8 and do not reach the floor region located below the drip collector 8 in an unwanted manner.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

1 Cleaning and/or disinfecting device
2 Rinsing container
3 Rinsing chamber
4 Loading opening
5 Lift door
6 Height direction
7 Frame
8 Drip collector
9 Transverse direction
10 Ball roller pull-out
11 Flat element
12 Large side
13 Motor unit
14 Electric motor
15 Drive shaft
16 Collection pan
17 Cut-out
18 Driver
19 Slot
20 Toothed wheel
21 Toothed belt
22 Wheel 23 Wheel
24 V-belt

What is claimed is:

1. A cleaning and/or disinfecting device, comprising:
a rinsing container having a rinsing chamber, the rinsing container having a loading opening for loading with washware to be cleaned;
a rinsing chamber door, by which the loading opening can be closed in a fluid-tight manner, wherein the rinsing chamber door is a lift door configured to be displaceable translationally in a height direction of the rinsing container; and
a drip collector arranged below the rinsing container in the height direction, the drip collector being configured to be displaced translationally in a direction running transversely to the height direction of the rinsing container, the drip collector being configured to be transitioned from a non-use position overlapping with the rinsing container to a use position protruding past the rinsing container on a loading opening side and from the use position back to the non-use position.

2. The cleaning and/or disinfecting device according to claim 1, wherein the drip collector comprises flat plate.

3. The cleaning and/or disinfecting device according to claim 2, wherein a large side of the flat plate, facing the rinsing container, has a slope.

4. The cleaning and/or disinfecting device according to claim 2, wherein the drip collector is configured as a trough, wherein the flat plate has a border strip on a rinsing chamber side.

5. The cleaning and/or disinfecting device according to claim 1, wherein the drip collector is mounted to be displaceable by ball roller pull-outs.

6. The cleaning and/or disinfecting device according to claim 1, wherein the drip collector is configured to be displaced manually between the use position and the non-use position.

7. The cleaning and/or disinfecting device according to claim 1, wherein the drip collector is configured to be displaced by a motor between the use position and the non-use position.

8. The cleaning and/or disinfecting device according to claim 7, wherein the drip collector is in operative connection with the motor operated separately by a user.

9. The cleaning and/or disinfecting device according to claim 1, wherein the lift door is configured to be displaced by a motor in operative connection with the lift door.

10. The cleaning and/or disinfecting device according to claim 9, wherein the drip collector is in operative connection with the motor.

11. The cleaning and/or disinfecting device according to claim 9, wherein the motor is operatively connected to a drive shaft, the drive shaft interacting with a force transmission member having a driver.

12. The cleaning and/or disinfecting device according to claim 10, wherein the motor is operatively connected to a drive shaft, the drive shaft interacting with a force transmission member having a driver.

13. The cleaning and/or disinfecting device according to claim 11, wherein the driver engages in a form-fitting manner in a receiver provided in the drip collector.

14. The cleaning and/or disinfecting device according to claim 13, wherein the receiver is a slot having a longitudinal extent exceeding a dimension of the driver in the longitudinal direction.

15. The cleaning and/or disinfecting device according to claim 11, further comprising a gear arrangement between the motor and force transmission member.

16. The cleaning and/or disinfecting device according to claim 13, further comprising a gear arrangement between the motor and force transmission member.

17. The cleaning and/or disinfecting device according to claim 11, wherein the force transmission member is one of a belt or a chain.

18. The cleaning and/or disinfecting device according to claim 13, wherein the force transmission member is one of a belt or a chain.

19. The cleaning and/or disinfecting device according to claim 15, wherein the force transmission member is one of a belt or a chain.

20. A method of reprocessing at least one surgical instrument, the method comprising:
loading washware to be cleaned in a rinsing container having a rinsing chamber, the rinsing container having a loading opening;
displacing a rinsing chamber door translationally in a height direction of the rinsing container, the rinsing chamber door being configured to close the loading opening in a fluid-tight manner; and
displacing a drip collector arranged below the rinsing container in the height direction translationally in a direction running transversely to the height direction of the rinsing container, the drip collector being configured to be transitioned from a non-use position overlapping with the rinsing container to a use position protruding past the rinsing container on a loading opening side and from the use position back to the non-use position.

* * * * *